United States Patent [19]
Schmid

[11] 3,988,346
[45] Oct. 26, 1976

[54] PYRAZOLINE COMPOUNDS USEFUL AS OPTICAL BRIGHTENERS

[75] Inventor: Horst Schmid, Reinach, Switzerland

[73] Assignee: Sandoz Ltd., Basel, Switzerland

[22] Filed: June 12, 1975

[21] Appl. No.: 586,350

[30] Foreign Application Priority Data
June 18, 1974 Switzerland.......................... 8311/74

[52] U.S. Cl............................. 260/310 D; 260/311; 252/301.27
[51] Int. Cl.²...................................... C07D 231/06
[58] Field of Search........................ 260/310 D, 311

[56] References Cited
FOREIGN PATENTS OR APPLICATIONS

| | | |
|---|---|---|
| 1,354,629 | 1/1964 | France |
| 291,734 | 5/1964 | Netherlands |
| 1,195,344 | 6/1970 | United Kingdom |
| 1,360,490 | 6/1974 | United Kingdom |

*Primary Examiner*—Donald B. Moyer
*Attorney, Agent, or Firm*—Gerald D. Sharkin; Richard E. Vila; Thomas C. Doyle

[57] ABSTRACT

Disclosed are optical brightening agents of formula I,

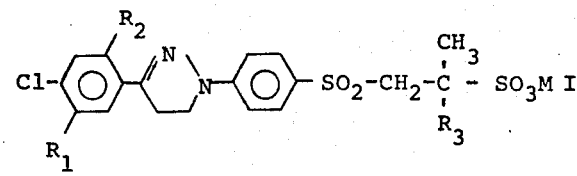

wherein
$R_1$ is hydrogen or chlorine,
$R_2$ is hydrogen or methyl,
$R_3$ is hydrogen or $C_{1-6}$alkyl, and
M is hydrogen or a non-chromophoric cation.

15 Claims, No Drawings

PYRAZOLINE COMPOUNDS USEFUL AS OPTICAL BRIGHTENERS

The invention relates to pyrazoline compounds.

According to the invention there are provided compounds of formula I,

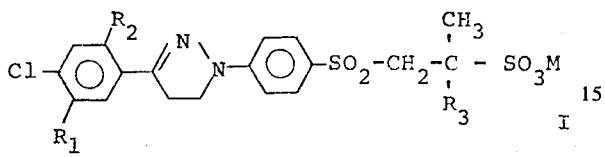

wherein
$R_1$ is hydrogen or chlorine,
$R_2$ is hydrogen or methyl,
$R_3$ is hydrogen or $C_{1-6}$ alkyl, and
M is hydrogen or a non-chromophoric cation.

Any alkyl as $R_3$, containing 3 or more carbon atoms, may be straight or branched. The preferred alkyls as $R_3$ are of 1 to 3 carbon atoms. The particularly preferred significances of $R_3$ are hydrogen and methyl.

Compounds of formula I are preferred in which either $R_1$ is chlorine and $R_2$ is methyl or $R_1$ and $R_2$ are both hydrogen.

Where M is a non-chromophoric cation, the exact significance thereof is not critical, it suitably being any cation conventional in the optical brightener art. As examples may be given the alkali-metal, e.g. lithium, sodium and potassium, cations, alkaline earth metal, e.g. calcium and magnesium, cations, and ammonium and substituted ammonium cations, e.g. of formula $R_5R_6R_7R_8N^+$ wherein $R_5$, $R_6$, $R_7$ and $R_8$, independently, signify hydrogen, $C_{1-3}$alkyl or $C_{2-4}$hydroxyalkyl. Where any of $R_5$ to $R_8$ signify hydroxyalkyl, at least one thereof is preferably hydrogen and the hydroxy group is preferably at least two carbon atoms remote from the nitrogen. Particular examples of cations of formula $R_5R_6R_7R_8N^+$ are ammonium, mono-, di- and tri-ethanolammonium, mono-, di- and tri-isopropanolammonium and tetramethylammonium. As will be appreciated, cations as M may be di- or polyvalent. However, for the sake of simplicity, M is shown in the formulae herein as being monovalent. The preferred cations as M are the alkali-metal and ammonium and substituted ammonium cations, particularly the alkalimetal cations, of which the sodium cation is most preferred.

As a preferred class of compounds provided by the invention may be given the compounds of formula Ia,

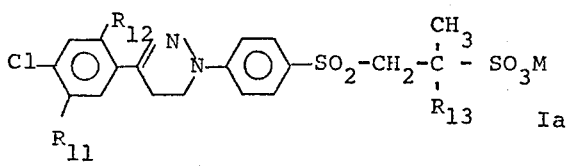

wherein either
$R_{11}$ and $R_{12}$ are both hydrogen,
or $R_{11}$ is chlorine, and
$R_{12}$ is methyl,
$R_{13}$ is hydrogen or methyl, and
$M_1$ is an alkali-metal, ammonium or substituted ammonium cation.

Of particular interest are compounds of formula Ia in which $R_{11}$ is chlorine, $R_{12}$ is methyl and $R_{13}$ is hydrogen and the compounds of formula Ia in which $R_{11}$ and $R_{12}$ are both hydrogen and $R_{13}$ is as defined above.

The invention also provides a process for the production of compounds of formula I, comprising
a. reacting a compound of formula II,

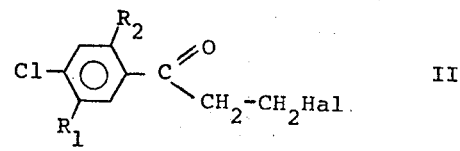

in which $R_1$ and $R_2$ are as defined above, and Hal is chlorine, bromine or iodine, with a compound of formula III,

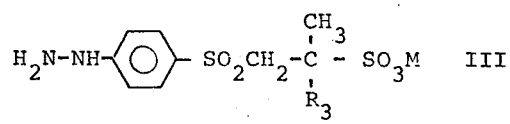

in which $R_3$ and M are as defined above, or
b. reacting a compound of formula IV,

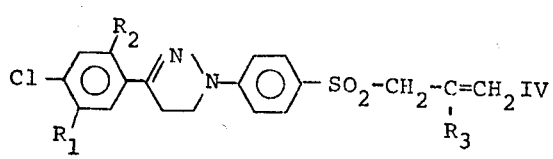

in which $R_1$, $R_2$ and $R_3$ are as defined above, with $M_2SO_3$, in which M is as defined above, in the presence of water.

Process a) is suitably carried out in conventional manner, for example in aqueous, aqueous/organic or organic medium, examples of suitable organic media being methanol, ethanol, isopropanol, acetic acid and dimethylformamide. Suitable reaction temperatures are from 20 to 200° C, preferably from 50° to 150° C. A suitable pH value is from 1 to 10.

Process b) is also suitably carried out in conventional manner. The reaction may be carried out in water alone or in aqueous/organic medium. Elevated temperatures are preferably employed, suitably the reflux temperature of the reaction medium or higher temperatures when carried out under superatmospheric pressure. The preferred compounds $M_2SO_3$ are the alkali-metal sulphites, particularly sodium sulphite.

The resulting compounds of formula I may be isolated and purified in conventional manner.

As will be appreciated, interconversion from one cation as M to another and from free acid to salt forms of the compounds, and vice versa, may be carried out in conventional manner.

The compounds of formulae II, III and IV are either known or may be produced from available starting materials in manner analogous to the production of known analogous compounds.

The compounds of formula I are optical brightening agents, being suitable for the brightening of substrates normally brightened using anionic brightening agents, e.g. substrates comprising or consisting of natural or regenerated cellulose and natural or synthetic polyamides. The particularly preferred use of the compounds is in the brightening of textile substrates, in for example, fibre, filament, yarn, woven, knitted or non-woven form, and consisting of synthetic polyamide. Conventional methods of application, e.g. exhaust, preferably acid exhaust, padding, acid shock and so-called "Thermosol", may be employed.

Conventional amounts of compounds of formula I may be employed, for example in the order of from 0.001 to 0.5%, preferably 0.05 to 0.4% by weight, based on the weight of the substrate.

The compounds of formula I may also be incorporated in non-ionic, or preferably anionic, detergent compositions. Based on the active ingredient in such compositions, the compounds of formula I are suitably employed in amounts of from 0.5 to 5%, preferably from 2 to 4%. Such composition may contain further conventional additives, such as phosphates, sulphates, dispersing agents, anti-foaming agents and the like.

Compounds closely similar to various compounds of the present invention but differing in having a straight alkylene chain as opposed to the branched alkylene chain of the present compounds are known, e.g. from Dutch Patent Applications 6902281 and 7102967. In comparison to such known compounds the compounds of the present invention, and particularly those indicated to be preferred, generally give brightenings of higher maximum whiteness. The compounds, particularly in alkali-metal salt form, have good solubility in water and the brightenings obtained have notable overall fastness properties.

The following Examples, in which all parts and percentages are by weight, and all temperatures in degrees centigrade, illustrate the invention.

EXAMPLE 1

394 g 4-hydrazinophenyl-(β-sulpho-iso-butyl)-sulphone are stirred together with 4.5 l water and 1.8 l methanol and the whole is adjusted to a pH of 3 with a 20% soda solution. It is then heated to boiling point and a solution of 232 g β-chloroethyl-4-chlorophenyl ketone is added drop-wise over 2 hours. The pH is kept at 2–3 by the addition of further 20% soda solution. After a total of 6–8 hours reaction time, during which time the pH is kept constant, the whole is cooled to 10° and the yellow precipitate filtered off. It is washed with a little cold methanol and recrystallised from 80% methanol. Pale yellow crystals which decompose at 315° are obtained of the compound of formula X,

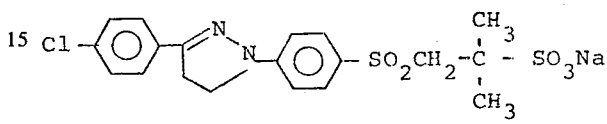

X

Absorption wave length in dimethylformamide λmax.=379nm

Emission wave length in dimethylformamide λmax.=443nm

Quantum yield $\Phi_{FL}$=0.89

The compound brightens nylon 6.6 fabric in a reddish nuance.

The hydrazine used as the starting product can be obtained as follows:

319 g acetylaminobenzene sulphinic acid in the form of a 2.2 l aqueous solution is adjusted to a pH of 8 with a 30% caustic soda solution and mixed with 264 g methallyl chloride. This is then heated to 70° with stirring over the course of one hour and the pH is kept at 9–10 by the addition of further 30% caustic soda solution. The reaction mixture is stirred for a total of 5 hours at reflux temperature, then cooled to 20° and the white precipitate is filtered. After recrystallising from ethanol, the compound melts at 145°–146° (uncorr.) and has the formula XI,

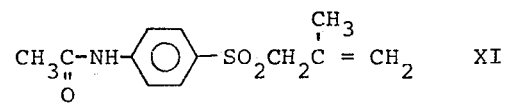

234 g methallylsulphonyl-4-acetanilide together with 139 g sodium sulphite and 680 cc water are heated to boiling point, with stirring, over the course of 5 hours, during which time a clear solution forms. This is then saponified with 850 cc concentrated hydrochloric acid for 2 hours at reflux temperature, after which it is cooled to 0° and diazotised with 79 g sodium nitrite.

The diazonium salt solution is reduced with 410 g sodium sulphite and 410 g soda to the hydrazine of formula XII,

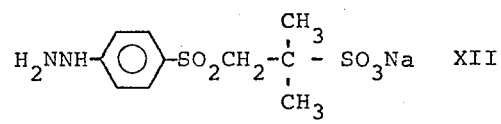

which can be further processed in the form of an aqueous suspension without isolation.

EXAMPLE 1a 40 g of the compound of formula XIII,

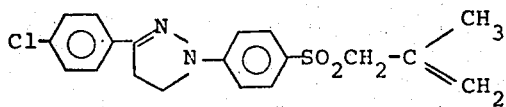

XIII with a melting point of 186°–188°, together with 14.8 g sodium sulphite in a mixture of 200 cc methyl cellosolve and 100 cc water are heated to boiling for 10 hours. 31 g of a pale yellow compound of formula X in Example 1 are obtained.

The following Table gives further examples of compounds of formula I which can be produced in the form of the sodium salts in a similar way to that described in Examples 1 and 1a. The Table also shows the substituents $R_1$, $R_2$ and $R_3$, the absorption and emission wave lengths, the quantum yield, decomposition temperature or fluoroescent shade in aqueous-alcoholic solution for these examples. In perfectly analogous manner, compounds of formula I, in which M is hydrogen or a cation other than sodium, may likewise be produced.

Application Example A

5 Parts of a white polyamide 6.6 fabric (Banlon) are washed in 250 parts of an aqueous solution containing

Application Example B

5 Parts of a white fabric consisting of polyamide 6 (Perlon tricot) are treated for 30 minutes at 90° in 200 cc of an aqueous solution (length of liquor 1:40) containing 0.05 g of the brightener of Example 4 and 0.1 parts 85% formic acid. After rinsing with cold water the fabric shows a brilliant brightening of violet nuance, compared with the untreated material.

If one of the compounds of Example 1 or 2 is used in place of the brightener of Example 4, brightenings of violet nuance are likewise obtained.

Application Example C

A fabric consisting of polyamide 66 is impregnated with a liquor which contains 5 g/liter of the optical brightener of Example 1 in the form of a 1% solution and 20 g/liter octylphenol pentaglycolether and 4 cc/liter 85% formic acid. After squeezing to a residual moisture of 80%, the fabric is dried for 45 seconds at 100° and then treated by the thermosol process for 30 seconds at 180°.

A brilliant brightened polyamide 66 fabric is obtained with a violet nuance. If one of the compounds of Example 2 or 4 is used in place of the compound from Example 1, similaar brilliant brightenings are obtained.

Application Example D

5 Parts of a white fabric consisting of polyamide 6.6 are treated at 40°–50° in 200 cc of an aqueous solution (length of liquor 1:40) contaning 0.05 g of the brightener from Example 1, then fixed in an acid bath (acetic or formic acid) at a pH of 3–3.5 and at 90°–100° for 2.5

Table

| Exp. No. | $R_1$ | $R_2$ | $R_3$ | Wave length max (nm) Absorption | Emission | (solvent) | Quantum yield $\Phi_{FL}$ | Decomposition temperature | Fluorescent shade in $H_2O$/alcohol |
|---|---|---|---|---|---|---|---|---|---|
| 2 | Cl | $CH_3$ | $Ch_3$ | 371 | 445.6 | dimethyl-formamide | 0.92 | 281–285° | |
| 3 | Cl | H | $CH_3$ | 376 | 458.7 | do. | 0.94 | over 300° | |
| 4 | H | H | H | 369 | 440 | dimethyl-formamide/water | 0.89 | | neutral blue |
| 5 | Cl | $CH_3$ | H | 370 | 443 | dimethyl-formamide | 0.89 | | violet blue | one part of a washing powder based on sodium dodecyl benzene sulphonate and 0.008 parts of the brightener of Example 1. The liquor is heated to 70° over 15 minutes and is kept at this temperature for 30 minutes. The fabric is then rinsed thoroughly in cold water and dried at 60°. In comparison to untreated material it shows a brilliant brightening of reddish violet nuance.

A suitable detergent contains, for example
20–30% sodium dodecyl benzene sulphonate
10–20% sodium tripolyphosphate
50–70% sodium sulphate In the above example if, in place of the 0.008 parts of the brightener from Example 1, the same quantity of a brightener of Example 2, 4 or 5 is used, a similar brilliant brightening of neutral violet nuance is obtained.

seconds. The fabric is then washed with water at 60°. A brilliant brightening of neutral blue nuance is obtained.

What is claimed is:

1. A compound of formula I, $$Cl-\underset{R_1}{\underset{|}{\bigcirc}}-\underset{R_2}{\overset{|}{\underset{N}{\bigcirc}}}-\bigcirc-SO_2-CH_2-\underset{R_3}{\overset{CH_3}{\underset{|}{C}}}-SO_3M$$

I wherein
- $R_1$ is hydrogen or chlorine,
- $R_2$ is hydrogen or methyl,
- $R_3$ is hydrogen or $C_{1-6}$alkyl, and
- M is hydrogen or a cation selected from the group consisting of alkali metal, alkaline earth metal and ammonium of the formula $R_5R_6R_7R_8N^+$ wherein $R_5$, $R_6$, $R_7$, and $R_8$, independently, signify hydrogen, alkyl of 1 to 3 carbon atoms or hydroxyalkyl of 2 to 4 carbon atoms.

2. A compound of claim 1, in which any alkyl as $R_3$ is of 1 to 3 carbon atoms.

3. A compound of claim 2, in which $R_3$ is hydrogen or methyl.

4. A compound of claim 1, in which either $R_1$ is chlorine and $R_2$ is methyl or $R_1$ and $R_2$ are both hydrogen.

5. A compound of claim 3, in which $R_1$ is chlorine and $R_2$ is methyl.

6. A compound of claim 5, in which $R_3$ is hydrogen.

7. A compound of claim 3, in which $R_1$ and $R_2$ are both hydrogen.

8. A compound of claim 7, in which $R_3$ is hydrogen.

9. A compound of claim 7, in which $R_3$ is methyl.

10. A compound of claim 1, wherein M is an alkali-metal, ammonium or substituted ammonium cation.

11. A compound of claim 10, in which M is the sodium cation.

12. A compound of claim 6, in which M is sodium.

13. A compound of claim 8, in which M is sodium.

14. A compound of claim 9, in which M is sodium.

15. A compound according to claim 1 wherein $R_5R_6R_7R_8N^+$ is ammonium, mono-, di-, or triethanolammonium, mono-, di- or tri-isopropanolammonium or tetramethylammonium.

* * * * *